(12) United States Patent
Bass et al.

(10) Patent No.: US 12,390,827 B1
(45) Date of Patent: Aug. 19, 2025

(54) LUMEN COATING METHOD AND APPARATUS

(71) Applicant: Biocoat, Incorporated, Horsham, PA (US)

(72) Inventors: Spencer Thomas Bass, Oreland, PA (US); Zichun Jacqueline Lu-Wright, Warminster, PA (US)

(73) Assignee: Biocoat, Incorporated, Horsham, PA (US)

( * ) Notice: Subject to any disclaimer, the term of this patent is extended or adjusted under 35 U.S.C. 154(b) by 0 days.

(21) Appl. No.: 18/771,245

(22) Filed: Jul. 12, 2024

Related U.S. Application Data

(63) Continuation-in-part of application No. 18/337,560, filed on Jun. 20, 2023, now Pat. No. 12,064,566.

(60) Provisional application No. 63/367,155, filed on Jun. 28, 2022.

(51) Int. Cl.
*B05C 11/10* (2006.01)
*A61M 25/00* (2006.01)
*B05C 3/09* (2006.01)
*B05C 11/06* (2006.01)

(52) U.S. Cl.
CPC ..... *B05C 11/1026* (2013.01); *A61M 25/0009* (2013.01); *A61M 25/0045* (2013.01); *B05C 3/09* (2013.01); *B05C 11/06* (2013.01); *A61M 2025/0047* (2013.01); *A61M 2207/10* (2013.01)

(58) Field of Classification Search
None
See application file for complete search history.

(56) References Cited

U.S. PATENT DOCUMENTS

| | | | | |
|---|---|---|---|---|
| 5,603,991 A * | 2/1997 | Kupiecki | ......... | A61M 25/0009 427/430.1 |
| 5,720,815 A * | 2/1998 | Swain | ..................... | B05C 3/109 118/500 |
| 5,725,667 A * | 3/1998 | Petropoulos | .............. | B05C 3/09 118/500 |
| 6,254,921 B1 * | 7/2001 | Chappa | ..................... | B05C 3/09 427/430.1 |
| 6,673,453 B2 | 1/2004 | Beavers et al. | | |
| 7,320,690 B2 | 1/2008 | Beavers et al. | | |
| 7,381,273 B2 * | 6/2008 | Collins | ..................... | B05C 3/09 118/423 |
| 8,162,877 B2 * | 4/2012 | Bonnette | ........... | A61M 25/0029 604/93.01 |
| 8,245,660 B2 * | 8/2012 | Dillon | ..................... | B05D 1/18 118/421 |
| 10,875,048 B2 * | 12/2020 | Surma | ....................... | B05C 3/10 |

(Continued)

*Primary Examiner* — Jethro M. Pence
(74) *Attorney, Agent, or Firm* — BakerHostetler

(57) ABSTRACT

A method for coating the lumen of a tube comprises the steps of inserting the distal opening of a tube into a first coating solution, drawing the first coating solution into the lumen of the tube, draining the first coating solution from the lumen leaving a film of the first coating solution on the lumen of the tube, and curing the first coating solution. This leaves a first coating on the lumen of the tube. A coating apparatus comprises a pallet, and one or more dip funnels. The pallet comprises a manifold and is configured to fluidically connect the manifold to one or more tubes. The one or more dip funnels are configured to hold a coating solution and are located below the pallet so that when the pallet is moved vertically, the one or more tubes are inserted into the dip funnels.

12 Claims, 4 Drawing Sheets

(56) References Cited

U.S. PATENT DOCUMENTS

| | | |
|---|---|---|
| 11,285,507 B2 * | 3/2022 | Choi ................. B05C 13/02 |
| 11,441,092 B2 | 9/2022 | Rhodes |
| 2003/0096131 A1 | 5/2003 | Beavers et al. |
| 2003/0203991 A1 | 10/2003 | Schottman |
| 2006/0129091 A1 * | 6/2006 | Bonnette ............. A61B 17/22 |
| | | 604/93.01 |
| 2007/0222132 A1 * | 9/2007 | Anderson ............. B05C 3/109 |
| | | 269/37 |
| 2011/0014386 A1 * | 1/2011 | Dillon ................. B05C 3/02 |
| | | 118/421 |
| 2011/0200828 A1 | 8/2011 | Li |
| 2017/0281907 A1 * | 10/2017 | Jelle ............... A61M 25/0023 |
| 2019/0070630 A1 * | 3/2019 | Surma .................. B05D 1/18 |
| 2019/0099777 A1 * | 4/2019 | Hackenberg ....... B05C 11/1042 |
| 2021/0220867 A1 * | 7/2021 | Choi ................. B05C 13/02 |
| 2023/0181870 A1 | 6/2023 | Hutar |
| 2023/0182163 A1 * | 6/2023 | Li ....................... B05C 3/10 |
| | | 427/430.1 |
| 2023/0191081 A1 | 6/2023 | Hutar |
| 2023/0270973 A1 * | 8/2023 | Hutar ................ A61M 25/005 |
| | | 604/48 |

* cited by examiner

LUMEN COATING METHOD AND APPARATUS

CROSS REFERENCE TO RELATED APPLICATIONS

This is a continuation-in-part application of U.S. patent application Ser. No. 18/337,560, filed Jun. 20, 2023, which claims the benefit of the provisional patent application of the same title, Ser. No. 63/367,155, filed on Jun. 28, 2022, the disclosures of each are incorporated by reference in their entirety.

BACKGROUND

Substrates such as tubes used for medical devices often benefit from having a lubricious coating because they allow the easy insertion into a patient and the passing of medical devices along the substrate. An example of a tube includes catheters which may be used for inserting and directing a device into a patient. Low friction exterior and lumen surfaces allow the catheter to be more easily maneuvered within a patient and facilitate passing guidewires and devices through the interior of the catheter. Previous catheters have used PTFE liners to provide a low friction lumen surface but suffer from stiffness and thick walls. A lubricious coating that can be applied to the lumen surface, exterior, or both of a catheter would allow a catheter to be produced that has thinner walls, stronger, and/or more flexible.

BRIEF SUMMARY

A method for coating the lumen of a tube comprises the steps of inserting the distal opening of a tube into a first coating solution, drawing the first coating solution into the lumen of the tube, draining the first coating solution from the lumen leaving a film of the first coating solution on the lumen of the tube, and curing the first coating solution. This leaves a first coating on the lumen of the tube.

A coating apparatus comprises a pallet, a manifold, and one or more dip funnels. The pallet is configured to fluidically connect the manifold to one or more tubes. The one or more dip funnels are configured to hold a coating solution and are located below the pallet so that when the pallet is moved vertically, the one or more tubes are inserted into the dip funnels.

These and other objects and advantages shall be made apparent from the accompanying drawings and the description thereof.

BRIEF DESCRIPTION OF THE FIGURES

The accompanying drawings, which are incorporated in and constitute a part of this specification, illustrate embodiments, and together with the general description given above, and the detailed description of the embodiments given below, serve to explain the principles of the present disclosure.

DETAILED DESCRIPTION

Figure 1:
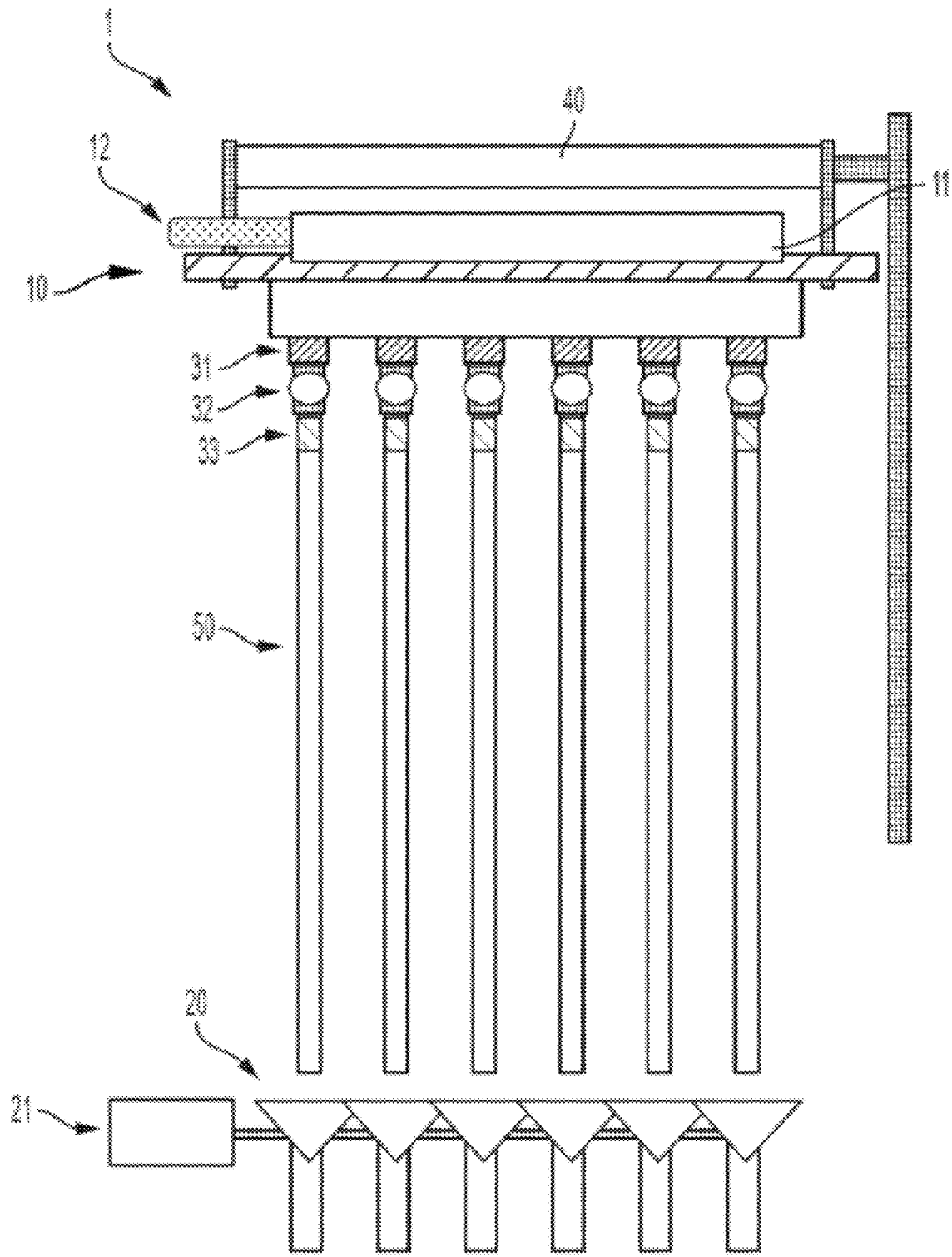
FIG. 1 is a diagram of an example coating apparatus.

Coating the lumen of a tube has multiple challenges such as preventing bubbles, making an even coating, not having the coating disintegrate, not swelling the tube, providing consistent results, and a process that is scalable to coat multiple tubes. This method provides the ability to independently coat the lumen and optionally the outer surface with one or more layers. A method for coating the lumen of a tube comprises the steps of inserting the distal opening of a tube into a first coating solution, drawing the first coating solution into the lumen of the tube, draining the first coating solution from the lumen leaving a film of the first coating solution on the lumen of the tube, and curing the first coating solution. This leaves a first coating on the lumen of the tube.

In some aspects, at least a portion of the tube is inserted into the first coating solution before or simultaneous with the step of drawing the first coating solution into the lumen of the tube. This allows the outside surface of the tube to be coated in the same step as the lumen while providing support and reduced buoyancy. In some aspects, the tube is inserted simultaneous with the drawing of the first coating solution into the lumen of the tube. This may result in the coating solution level inside the tube to remain at the same level as that of the coating solution outside the tube. The first coating solution may be drained from the lumen before, during, or after at least a portion of the tube is removed from the first coating solution. This leaves a film of the first coating solution on the lumen and the outside surface of the tube. After the first coating solution is cured there will be a first coating on the lumen and outside surface of the tube.

In some aspects, the distal opening of a tube which has a first coating on the lumen and outside surface is inserted into a second coating solution. The second coating solution is drawn into the lumen of the tube. This allows the lumen of the tube to be coated with a second coating. The second coating solution is drained from the lumen leaving a film of the second coating solution on the lumen of the tube. The second coating solution is cured, leaving a second coating on the lumen of the tube. The second coating is on top of the first coating on the lumen of the tube.

In some aspects, at least a portion of the tube which has a first coating on the lumen is inserted into the second coating solution before or simultaneous with the step of drawing the second coating solution into the lumen of the tube while providing support and reduced buoyancy. This allows the outside surface of the tube to be coated in the same step as the lumen. In some aspects, the tube is inserted simultaneous with the drawing of the second coating solution into the lumen of the tube. This may result in the coating solution level inside the tube to remain at the same level as that of the coating solution outside the tube. The second coating solution may be drained from the lumen before, during, or after a least a portion of the tube is removed from the second coating solution. This leaves a film of the second coating solution on the lumen and the outside surface of the tube. After the second coating solution is cured there will be a second coating on top of the first coating on the lumen and there is a second coating on the outside surface of the tube.

In some aspects, the distal opening of a tube which has a first coating is inserted into a second coating solution. The second coating solution is drawn into the lumen of the tube. This allows the lumen of the tube to be coated with a second coating. The second coating solution is drained from the lumen leaving a film of the second coating solution on the lumen of the tube. The second coating solution is cured, leaving a second coating on the lumen of the tube. The second coating is on top of the first coating on the lumen of the tube and there is a first coating on the outside surface of the tube.

In some aspects, at least a portion of the tube which has a first coating on the lumen and outside surface is inserted into the second coating solution before or simultaneous with the step of drawing the second coating solution into the lumen of the tube. This allows the outside surface of the tube to be coated in the same step as the lumen. In some aspects, the tube is inserted simultaneous with the drawing of the second coating solution into the lumen of the tube. This may result in the coating solution level inside the tube to remain at the same level as that of the coating solution outside the tube. The second coating solution may be drained from the lumen before, during, or after a least a portion of the tube is removed from the second coating solution. This leaves a film of the second coating solution on the lumen and the outside surface of the tube. The second coating is on top of the first coating on the lumen and outside surface of the tube.

The tube is put into contact with the first or second coating solution. This may be by inserting the distal opening of the tube into the coating solution and drawing the coating solution into the lumen of the tube or by dipping the tube into the coating solution. The distal opening of the tube is the opening of the tube that is opposite that which is being held. After the coating solution is withdrawn from the tube, a film of the coating solution will remain on the tube which allows it to be cured to form a coating. The viscosity, concentration, release speed, withdraw rate, and dwell time will affect the thickness of the coating after it is cured. In some aspects, the coating solution is drained from the lumen by flowing a gas through the lumen. Examples of the gas include, but are not limited to air, $N_2$, argon, $CO_2$, and $O_2$. The gas flow may also affect the thickness of the coating. In some aspects, gas can be pulled through the inner lumen and manifold via a pressure gradient. This pressure gradient can be achieved via a vacuum pump, vacuum tank, venturi pump or similar device.

In some aspects, a cleaning solution may be flowed through the lumen or on the surface of the tube to clean before the first or second coating. Examples of a cleaning solution include a short chain hydrocarbon, a short chain alcohol and/or water, or detergent and water. Examples of the short chain hydrocarbons include hexane(s), heptane(s), and octane(s). Examples of the short chain alcohol include ethanol, propanol, isopropanol, 1-butanol, isobutanol, butan-2-ol, tert-butanol, and combinations thereof. Examples of the detergent include Alconx Detonox, Alconx Liquinox, Ecolab Neutral Detergent, and ProClense plus Instrument Detergent which can be applied at a temperature range of 20-100° C., such as 60-80° C. The cleaning solution may clean off the coating to allow a better adhesion by the first coating.

In some aspects, the first coating solution comprises a mixture of polyaziridine and either polyurethane or polyacrylate, and a short chain alcohol.

The polyaziridine is a cross linker, such as trimethylolpropane tris(2-methyl-1-aziridine propionate) (TMAZ), N,N'-(methylenedi-p-phenylene)bis(aziridine-1-carboxamide) (DAZ), trimethylolpropane bis(2-methyl-1-aziridine propionate), pentaerythritol bis(3-(1-aziridinyl) propionate, pentaerythritol tris(3-(1-aziridinyl) propionate (TAZ), pentaerythritol tetrakis(3-(1-aziridinyl) propionate. Polyfunctional aziridines are known crosslinkers in thermal cure processes. In some aspects, the cross linker is selected from trimethylolpropane tris(2-methyl-1-aziridine propionate) (TMAZ), N,N'-(methylenedi-p-phenylene)bis (aziridine-1-carboxamide) (DAZ), pentaerythritol tris(3-(1-aziridinyl) propionate (TAZ). In some aspects, the cross linker is trimethylolpropane tris(2-methyl-1-aziridine propionate) (TMAZ).

Examples of the first coating solution polyurethane include Baymedix CD104; NeoRez™ R-960, R-966, R-2005, R-2180; NeoPac R-9036, E-125; and Witcobond W374 or 737, which are an aliphatic urethane water emulsions. In some aspects, the first coating solution polyurethane comprises NeoRez™ R-966, Witcobond W374, or Witcobond 737. In some aspects, the polyurethane has solids content of 1-15% by weight. In some aspects, the first coating solution is an aliphatic urethane emulsion in water with about 33% solids and a pH of 7.5-8.0. The polyurethane is water based and miscible with isopropyl alcohol. In some aspects, the polyurethane has no heavy metals. In some aspects, the polyurethane has a strong adhesion; it has a fully formulated peel tape value of between 2B-5B on plastics and steels. The peel tape value is measured according to ASTM D-3359. The free film properties of the polyurethane also include a hardness of 35 on D shore scale and an ultimate elongation percent of 150-300, more preferably 200-250.

Examples of the first coating solution polyacrylate copolymer include methacrylate, ethyl acrylate, propyl acrylate, butyl acrylate, and mixtures thereof. In some aspects, the polymer comprises methacrylate of the structure:

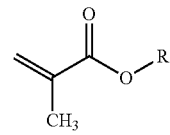

where R is an optionally substituted $C_1$-$C_{20}$ alkyl. In some embodiments, R may be methyl, ethyl, or butyl. Optionally, the copolymer will contain monomers such as ethylhexyl, isodecyl, dodecyl or others that contribute to a low glass temperature copolymer. The copolymer also contains monomers with some hydrophilic character to provide good interaction with the second coating solution and polymer. Examples include hydroxyethyl methacrylate and N-vinylpyrrolidone monomers. In some embodiments, the polyacrylate copolymer comprises monomers selected from hydroxyethyl methacrylate, N-vinylpyrrolidone, butyl acrylate, methyl methacrylate, and mixtures thereof. In some embodiments, the polyacrylate copolymer comprises hydrophilic monomers selected from hydroxyethyl methacrylate and N-vinylpyrrolidone and acrylate monomers selected from butyl acrylate and methyl methacrylate.

The short chain alcohol helps the first coating solution flow to coat the surface of the substrate. Examples of the short chain alcohol include ethanol, propanol, isopropanol, 1-butanol, isobutanol, butan-2-ol, tert-butanol, and combinations thereof. In some aspects, the first coating solution comprises 10%-85% of the short chain alcohol, such as 10%-20%, 20%-40%, 20%-30%, 30%-40%, 40%-50%, 50%-60%, 60%-70%, 70%-80%, and 80%-85%.

In some aspects, the first coating solution has a viscosity of 10-100 centipoise, such as 10-20, 20-30, 30-40, 40-50, 50-60, 60-70, 70-80, 80-90, and 90-100. In some embodiments, the viscosity is 30-60 centipoise. In some aspects, the first coating solution has a solids content of from 1% to 15%. In some aspects the first coating solution has a solids content of from 5% to 10%.

The first coating solution is cured with heat to form the first coating by crosslinking the polymers. The second coating solution is cured with heat to form the second coating by crosslinking the polymers. In some aspects, the first coating solution is cured before the second coating is applied. In some aspects, the first coating and second coating are cured simultaneously. Curing may be at a temperature of at least 22° C., such as 22° C.-120° C., 22° C.-25° C., 25° C.-30° C., 30° C.-35° C., 35° C.-40° C., 40° C.-45° C., 45° C.-50° C., 50° C.-55° C., 55° C.-60° C., 60° C.-65° C., 65° C.-70° C., 70° C.-75° C., 75° C.-80° C., 80° C.-85° C., 85° C.-90° C., 90° C.-95° C., 95° C.-100° C., 100° C.-105° C., 105° C.-110° C., 110° C.-115° C., and 115° C.-120° C. Curing includes the removal of solvent and/or chemical change, such as polymerization and/or crosslinking.

In some aspects, the first coating solution additionally comprises a zirconate or titanate such as tetra (2,2 diallyloxymethyl)butyl zirconate; di(ditridecyl)phosphito zirconate; zirconium IV bis octanolato, cyclo (dioctyl)-7-pyrophosphate-O, O; Tetraisopropyl di(dioctyl)phosphito titanate; and titanium IV bis octanolato, cyclo (dioctyl)-7-yrophosphate-O, O. In some aspects, the first coating solution additionally comprises a zirconate. In some aspects, the zirconate is selected from tetra (2,2 diallyloxymethyl)butyl zirconate; di(ditridecyl)phosphito zirconate; zirconium IV bis octanolato, cyclo (dioctyl)-7-yrophosphate-O, O. In some aspects, the zirconate is tetra (2,2 diallyloxymethyl) butyl zirconate.

In some aspects, the second coating solution comprises polysaccharide and/or polyacrylic acid. Examples of polysaccharides include hyaluronic acid and its alkali metal salts, chondroitin sulfate, heparin, hydroxypropyl methyl cellulose, carboxymethyl cellulose, and combinations of two or more of these.

Polyacrylic acids act a reinforcing agent. Examples of polyacrylic acids include polyacrylic acid, polymethacrylic acid, and copolymers of acrylic acid, of methacrylic acid, 2-ethylacrylic acid, 2-propylacrylic acid with such other co-monomers as 2-vinylpyrrolidinone, vinyl esters of aldonic acids, acrylamide, methacrylamide, N-methylol acrylamide, N-methylol methacrylamide, and N-alkyl acrylamide or methacrylamide, where the alkyl group may be methyl, ethyl, or propyl. In some embodiments, the molecular weight of the polyacrylic acid is from about 200K to 300K, such as from 200K to 210K, 210K to 220K, 220K to 230K, 230K to 240K, 240K to 250K, 250K to 260K, 260K to 270K, 270K to 280K, 280K to 290K, 290K to 300K, 300K to 310K, 310K to 320K, 320K to 330K, 330K to 340K, 340K to 350K, 350K to 360K, 360K to 370K, 370K to 380K, 380K to 390K, 390K to 400K, 400K to 410K, 410K to 420K, 420K to 430K, 430K to 440K, and 440K to 450K. In some aspects, the polyacrylic acid has a molecular weight of from about 240K to 250K. The molecular weight is determined via GPC.

In some aspects, the second coating solution comprises a polyacrylic acid and a polysaccharide. In some aspects, the second coating solution comprises polyacrylic acid and hyaluronic acid.

In some aspects, the second coating solution additionally comprises a crosslinker. A crosslinker in the second coat can improve durability of the coating in repeated stressing, surprisingly without significant loss of lubricity. Examples of crosslinkers include polyaziridines, polyepoxides, polyisocyanates, polycarbodiimide (tradename: NeoResins XL-1), 1,4-butanediol diglycidyl ether (BDDE), formaldehyde, urea/formaldehyde condensates and melamine/formaldehyde condensates, divalent or polyvalent cation salts, and other such reagents as will be apparent to one skilled in the art. In some aspects, the crosslinker is a polyaziridine.

In some aspects, the top-coat solution has a viscosity of 400-1300 centipoise, such as 400-500, 500-600, 600-700, 700-800, 800-900, 900-1000, 1000-1100, 1100-1200, and 1200-1300. In some aspects, the top-coat solution has a viscosity of 460-900 centipoise. In some aspects, the top-coat has a pH of 4 to 7, such as 4-5, 5-6, and 6-7. In some aspects, the top-coat has a pH range of 4.0 to 4.7, such as 4.1 to 4.2, 4.2 to 4.3, 4.3 to 4.4, 4.4 to 4.5, 4.5 to 4.6, and 4.6 to 4.7.

In some aspects, the second coating solution has a total solids by weight of about 0.5 to about 2.5%. In some aspects, the second coating solution has a total solids of about 0.5% to about 0.7%.

In some aspects, the tube is a catheter.

Apparatus

Figure 4:
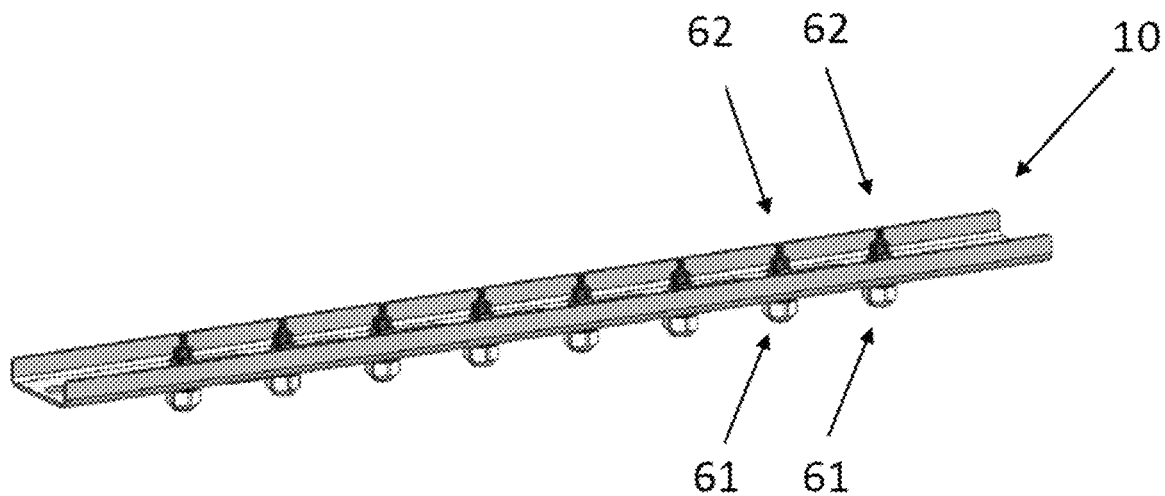
FIG. 4 is a diagram of an embodiment of a pallet.

A coating apparatus may be used to make it easier to draw the coating solutions into the lumen of a tube and insert the tube into the coating solutions. It may facilitate simultaneously coating multiple tubes. FIG. 1 shows an example coating apparatus (1) which comprises a pallet (10), a manifold (11), and one or more dip funnels (20). The pallet is configured to fluidically connect the manifold (11) to one or more tubes (50). The one or more dip funnels (20) are configured to hold a coating solution and are located below the pallet (10) so that when the pallet (10) is moved along the vertical axis, the one or more tubes (50) are inserted into the dip funnels (20). The connection fitting (12) connects the source of gasses or vacuum to the manifold (11). In some embodiments, the manifold is directly connected to the tubes. In some embodiments, the pallet connects the manifold and the tubes. FIG. 4 shows an example of the pallet (10) and the first fluidic coupling (61) which may attached to the tubes and second fluidic coupling (62) which may attach to the manifold.

In some aspects, the apparatus is configured for coating one or more tubes. Examples of the tubes include catheters. In some aspects, the one or more tubes are catheters.

In some aspects, the apparatus further comprises a dip rail (40). The dip rail (40) is attached to the pallet and is configured to move the pallet vertically, so the one or more tubes are inserted into the dip funnels. In some aspects, the dip funnels are fluidically connected to a reservoir (21) that allows the levels of the coating solution to remain relatively constant.

The pallet connects the tubes and manifold and fluidically connects the manifold to one or more of the tubes. Gas flow regulators (31), valves (32), level indicators (33), and combinations thereof may be attached to the pallet. The pallet (10) is attached to the dip rail (40) which holds the pallet and is used to move the pallet vertically. The pallet may be configured to rotate or spin the tubes which may facilitate curing, such as by ultra-violet light. The dip rail (40) may also be configured to transfer the pallet into a cure chamber or between transfer locations.

The manifold is configured to fluidically connect the gas flow or vacuum to the one or more tubes via the connection fitting. This gas flow or vacuum allows the coating solutions to be drawn into the tube or pushed out of the tube. Examples of mechanisms to provide a vacuum include syringe, syringe pump, vacuum pump, diaphragm pump, peristaltic pump, and venturi pump. In some aspects, between the manifold and the one or more tubes is one or more gas flow regulator, which fluidically connects the two. The gas flow regulators may be fluidically connected between the manifold and the pallet or between the pallet and the tubes. These gas flow regulators allow control of the gas flow or vacuum to individual tubes. Examples of gas flow regulators include, but are not limited to air flow control valves, air flow meters, pressure regulators, variable valves, pinch valves, varied tube/pipe/opening sizing such as flow control orifices and pressure relief valves. In some aspects, between the one or more tubes and the gas flow regulator are valves. These valves allow the gas flow or vacuum to individual tubes to be turned off or on. Examples of valves include, but are not limited to 3-way stop cock, solenoid valves, check valves, air flow control valves, modular air directional control valves and other valves of the sort. In some aspects, gas flow regulators are used to control the gas flow or vacuum to the manifold. Examples of gas flow regulators include, but are not limited to air flow control valves, air flow meters, pressure regulators, variable valves, pinch valves, varied tube/pipe/opening sizing such as flow control orifices, pressure relief valves.

In some aspects, the connection fitting is an air tight fitting that allows an operator or machine to easily attach and detach lines as it transfers to the cure chamber. Examples of connection fittings include AseptiQuick, Banjo fittings, Luer locks, Quickseal, barb fittings, blind mate connections, push-to-connect, valved couplers, quick disconnect couplings, Ring-lock quick disconnect couplings, Tru-flate quick disconnect couplings, Grip-lock couplings, Cam and Groove couplings, Twist Claw couplings. The connection fitting can optionally be closed to gas flow when disconnected or can be configured with a valve for ease of controlling flow direction.

In some aspects, the apparatus comprises level indicators (33) configured to monitor coating solution in each of the one or more tubes. Examples of level indicators include ultrasonic/sonic sensor/transmitter, laser sensor/transmitter, IR sensor/transmitter, bubble sensor, vision sensor, vision system, electrode electromagnetic flow sensor, pressure or vacuum sensor/switch/transducers, float valve/sensor, level switch, thermocouple, and resistance/capacitance. Level indicators may be located near the top of the tubes to sense when the level of the coating solution has coated all or substantially all of the tube.

In some aspects, the apparatus is configured so that the pallet and the one or more tubes may be transferred into a cure chamber via the dip rail or separate transfer arm. This allows the coatings on the tubes to be cured without having to remove each tube from the pallet. The apparatus may be used in a dip station which holds the pallet and dip funnels. It allows the pallet to dip the tubes into the dip funnels.

Figure 2:
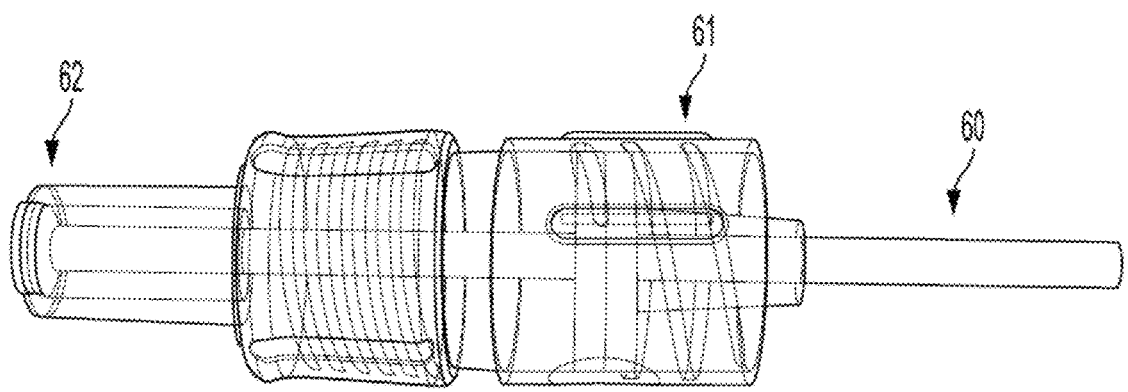
FIG. 2 is a diagram of an embodiment of a masking tube with fluidic connectors.
Figure 3:
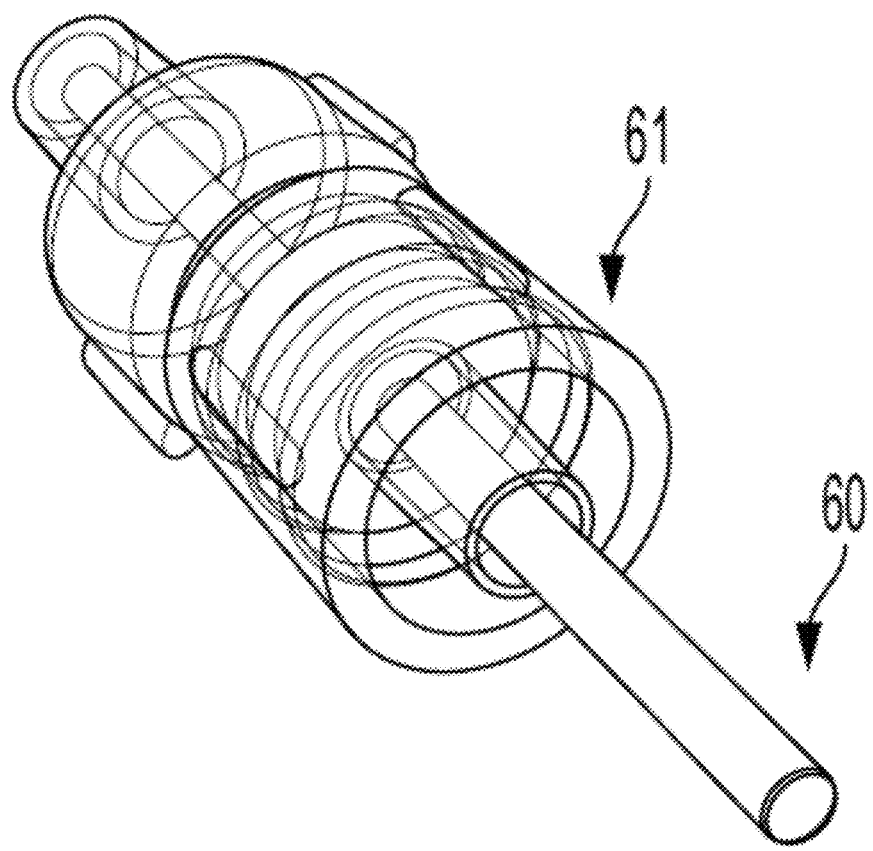
FIG. 3 is a diagram of an embodiment of a masking tube with fluidic connectors.

In some embodiments, a masking tube is placed within the tube to create a discrete lumen coating length along one end of the tube. A column of air between the inner surface of the tube and the outer surface of the masking tube prevents coating ingress along the length of this interface. The masking tube may be various lengths, such as 5 mm to 10 cm or longer. The length of the masking tube determines the length of the uncoated lumen of the tube. The masking tube fluidically connects the tube and the manifold. FIGS. 2 & 3 show the masking tube (60) and the first fluidic coupling (61). The first fluidic coupling (61) is between the masking tube and the tube. The second fluidic coupling (62) between the masking tube and the manifold allows for gas flow, vacuum flow, and/or coating solutions to pass through the masking tube. Examples of fluidic connections include Tuohy Borst, Luer locks, collet fitting, gasket fittings AseptiQuick, Banjo fittings, Luer locks, Quickseal, barb fittings, blind mate connections, push-to-connect, valved couplers, quick disconnect couplings, Ring-lock quick disconnect couplings, Tru-flate quick disconnect couplings, Grip-lock couplings, Cam and Groove couplings, Twist Claw couplings. Examples of materials for the masking tube include stainless steel, HDPE, polypropylene, polyurethane, PEBA, PTFE and other similar materials. In some aspects, the first and/or second fluidic couplings are molded into the masking tube to form a single piece.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

Where present, all ranges are inclusive and combinable. That is, references to values stated in ranges include every value within that range. For example, a range defined as from 400 to 450 ppm includes 400 ppm and 450 ppm as independent embodiments. Ranges of 400 to 450 ppm and 450 to 500 ppm may be combined to be a range of 400 to 500 ppm.

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art. Furthermore, features from separate lists can be combined; and features from the examples can be generalized to the whole disclosure.

EXAMPLES

Example 1

A bilaminar coating of the inner, outer and distal surfaces of a tube is begun with a distal opening of the tube being placed into the basecoat solution (first coating solution) at a distance that allows for at least the volume of the inner volume of the tube to be filled without air entrainment within the inner volume and is less than the full length of the tube. The basecoat solution is then pulled up the inner volume of the tube until it reaches the distance that the inner lumen is to be coated and is held in place utilizing a valve. The tube is then dipped into the basecoat solution at a rate between 0.1 in/sec and 1.5 in/sec to the desired outer surface coating length. The valve holding solution is released and the tube is withdrawn at a rate between 0.1 in/sec and 1.5 in/sec. The tube is then placed into a cure chamber where it is cured for 5-15 mins with gas flow to the inner lumen of the tube at a volumetric flow of 1 to 180 Standard Cubic Feet per Hour (SCFH). After this the topcoat (second coating solution) can be applied. The tube is placed into the topcoat at a distance that allows for at least the volume of the inner volume of the tube to be filled without air entrainment within the inner volume and is less than the full length of the tube. The topcoat solution is then pulled up the inner volume of the tube until it reaches the distance that the inner lumen is to be coated and is held in place utilizing a valve. The tube is then dipped into the topcoat solution at a rate between 0.1 in/sec and 1.5 in/sec to the desired outer surface coating length. The valve holding solution is released and the tube is withdrawn at a rate between 0.1 in/sec and 1.5 in/sec. The tube is then placed into a cure chamber where it is cured for 10-60 mins with gas flow to the inner lumen of the tube at a volumetric flow of 1 to 180 Standard Cubic Feet per Hour (SCFH). Finally, the tube is removed from the cure chamber.

What is claimed is:

1. A coating apparatus comprising a pallet, a manifold, and one or more dip funnels;
   wherein the pallet is configured to fluidically connect the manifold to the lumen of the one or more tubes;
   wherein the one or more dip funnels are configured to hold a coating solution and located below the pallet so that when the pallet is moved vertically, the one or more tubes are inserted into the dip funnels,
   wherein the manifold is configured to provide gas flow or vacuum to the lumen of the one or more tubes.

2. The apparatus of claim 1, wherein the one or more tubes are catheters.

3. The apparatus of claim 1, further comprising a dip rail, wherein the dip rail is attached to the pallet and is configured to move the pallet vertically, so the one or more tubes are inserted into the dip funnels.

4. The apparatus of claim 1, wherein the manifold is configured to provide the vacuum which is provided by a mechanism selected from syringe, syringe pump, vacuum pump, and venturi pump.

5. The apparatus of claim 1, wherein the manifold is fluidically connected to one or more gas flow regulators.

6. The apparatus of claim 5, wherein between the one or more tubes and the one or more gas flow regulators are valves.

7. The apparatus of claim 1, wherein the manifold is fluidically connected to one or more gas flow regulators and the one or more gas flow regulators are fluidically connected to the lumen of the one or more tubes.

8. The apparatus of claim 7, wherein the one or more gas flow regulators are fluidically connected between the manifold and the pallet, and the pallet is fluidically connected to the lumen of the one or more tubes.

9. The apparatus of claim 7, wherein between the one or more tubes and the gas flow regulator are valves.

10. The apparatus of claim 1, further comprising level indicators configured to monitor the coating solution in the lumen of each of the one or more tubes.

11. The apparatus of claim 10, wherein the level indicators are selected from ultrasonic/sonic sensor/transmitter, laser sensor/transmitter, IR sensor/transmitter, bubble sensor, vision sensor, vision system, electrode electromagnetic flow sensor, pressure or vacuum sensor/switch/transducers, float valve/sensor, level switch, thermocouple, and resistance/capacitance sensor.

12. The apparatus of claim 1, configured so that the pallet and the one or more tubes is capable of being placed into a cure chamber.

* * * * *